United States Patent [19]

Jung

[11] Patent Number: 4,894,371
[45] Date of Patent: * Jan. 16, 1990

[54] 3-SUBSTITUTED-AMINOMETHYL CEPHALOSPORIN DERIVATIVES

[75] Inventor: Frederic H. Jung, Rilly la Montagne, France

[73] Assignee: ICI Pharma, Cergy Cedex, France

[*] Notice: The portion of the term of this patent subsequent to Jul. 7, 2004 has been disclaimed.

[21] Appl. No.: 940,161

[22] Filed: Dec. 9, 1986

Related U.S. Application Data

[63] Continuation of Ser. No. 800,112, Nov. 20, 1985, abandoned.

[30] Foreign Application Priority Data

Nov. 29, 1984 [EP] European Pat. Off. ......... 84402449.7

[51] Int. Cl.$^4$ .................. C07D 501.18; A61K 31/545
[52] U.S. Cl. .................................. 514/202; 514/201; 540/222; 540/221
[58] Field of Search ............... 540/222, 221, 215, 201, 540/202

[56] References Cited

U.S. PATENT DOCUMENTS

| | | | |
|---|---|---|---|
| 4,278,793 | 7/1981 | Dürckheimer et al. | 540/227 |
| 4,499,088 | 2/1985 | Takaya et al. | 514/202 |
| 4,678,781 | 7/1987 | Jung | 540/227 |

FOREIGN PATENT DOCUMENTS

| | | |
|---|---|---|
| 0018155 | 4/1980 | European Pat. Off. |
| A127992 | 12/1984 | European Pat. Off. |
| 1155493 | 6/1969 | United Kingdom |
| 2068958 | 2/1981 | United Kingdom |
| 2071664 | 3/1981 | United Kingdom |
| 2105719 | 9/1982 | United Kingdom |
| 2103205 | 2/1983 | United Kingdom |

OTHER PUBLICATIONS

Merck Index, Entries 1899, 1902, 1905, 1908 and 1916 (1983: Merck and Co.; Rahway, N.J.) pp. 268–272.
Angew. Chem. Int. Ed. Engl. 24 (1985) pp. 180-20-2-Durckheimer et al.
Heterocycles, vol. 13, 1979, pp. 197–202-Kishi

*Primary Examiner*—Nicholas S. Rizzo
*Attorney, Agent, or Firm*—Cushman, Darby & Cushman

[57] ABSTRACT

An antibacterial cephalosporin derivative of the formula I:

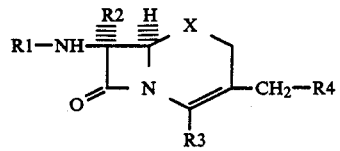

in which X is S,O,CH$_2$ or SO; R2 is hydrogen, methoxy or formylamino; R3 is carboxy or a biodegradable ester thereof; R1 represents a variety of groups known in the cephalosporin art and R4 represents a group NR42R43 wherein R42 is hydrogen, lower alkyl or benzyl and R43 is one of a group of neutral heterocyclic species defined in the specification. Pharmaceutical compositions, manufacturing processes and intermediates are also described. In a specific embodiment, 3-substituted aminomethyl cephalosporin derivatives in which X is S or SO are disclosed.

9 Claims, No Drawings

3-SUBSTITUTED-AMINOMETHYL CEPHALOSPORIN DERIVATIVES

This is a continuation of application Ser. No. 800,112, filed Nov. 20, 1985, which was abandoned upon the filing hereof.

This invention relates to cephalosporin derivatives which have antibacterial activity.

According to the invention there is provided a cephalosporin derivative of the formula I (formulae given hereinafter) in which X is sulphur, oxygen, methylene or sulphinyl (R or S configuration);

—R1 is of the formula II, III, IV, V, VI, VII or VIII in which R5 and R6, same or different, are hydrogen, halogen, cyano, hydroxy, carboxy, pyridyl, (1–6C)alkyl, (1–6C)aminoalkyl, (1–6C)hydroxyalkyl, (2–6C)alkoxycarbonyl, (2–10C)alkylaminoalkyl, (3–15C)dialkylaminoalkyl, or phenyl optionally substituted by 1 or 2 radicals selected from halogen, nitro, amino, hydroxy, carboxy, cyano, (1–6C)alkyl and (2–6C)alkoxycarbonyl;

R7 is carboxy, (2–6C)alkoxycarbonyl, benzyloxycarbonyl, carbamoyl, (2–6C)alkylcarbamoyl, (3–8C)dialkylcarbamoyl, carbazoyl, cyano or (2–6C)alkoxycarbonylamino;

R8 is hydrogen, (1–4C)alkyl, (1–4C)alkoxy, (2–5C)alkanoyl, (1–4C)alkylthio, (1–4C)alkanesulphinyl, (1–4C)alkanesulphonyl, phenyl, benzoyl, carboxy, (2–6C)alkoxycarbonyl, benzyloxycarbonyl, carbamoyl, carbazolyl, cyano, (2–5C)alkenyl, sulphamoyl, (1–4C)hydroxyalkyl, (2–4C)carboxyalkyl, benzyl, hydroxyphenyl, [(1–4C)alkoxy]phenyl, pyridyl or (methylthio)thiadiazolyl;

R9 is hydrogen, (1–6C)alkyl or phenyl;

R10 is of the formula IX, X, or XI;

R11 is 2-aminothiazol-4-yl or 2-aminooxazol-4-yl each optionally substituted in the 5-position by fluorine, chlorine or bromine, or R11 is 5-aminoisothiazol-3-yl, 5-amino-1,2,4-thiadiazol-3-yl, 3-aminopyrazol-5-yl, 3-aminopyrazol-4-yl, 2-amino-pyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R12 is hydrogen, (1–6C)alkyl, (3–8C)cycloalkyl, (1–3C)alkyl(3–6C)cycloalkyl, (3–6C)cycloalkyl(1–3C)alkyl, (3–6C)alkenyl, (5–8C)cycloalkenyl, (3–6C)alkynyl, (2–5C)alkylcarbamoyl, phenylcarbamoyl, benzylcarbamoyl, triphenylmethyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkylamino(2–6C)alkyl, (2–8C)dialkylamino(2–6C)alkyl, (1–5C)cyanoalkyl, (1–4C)azidoalkyl, (2–5C)ureidoalkyl, 3-amino-3-carboxypropyl, 2-(amidinothio)ethyl, 2-(N-aminoamidinothio)ethyl, tetrahydropyran-2-yl, thietan-3-yl or 2-oxotetrahydrofuran-3-yl, or —R12 is of the formula —(CH$_2$)$_n$—R15 in which n is 1 to 4 and R15 is piperidino, pyrrolidino, morpholino, piperazino or N-methylpiperazino, each value of R15 being optionally substituted by (1–4C)alkyl, phenyl or benzyl, or —R12 is of the formula —(CH$_2$)$_m$—W-R16 in which m is 0 to 3, W is sulphur or a direct bond, and R16 is phenyl or pyridinio(1–4C)alkylene or R16 is pyridyl, imidazolyl, 1,3,4-thiadiazolyl, tetrazolyl, 1-(1–4C)alkyltetrazolyl, thiazolyl, isothiazolyl or isoxazolyl in which the link with W is via a carbon or uncharged nitrogen, each value of R16 being optionally substituted, where possible, by one or two groups selected from (1–4C)alkyl, amino, hydroxy, carboxy, carbamoyl, nitro, (2–5C)alkoxycarbonyl, cyano and sulpho, or —R12 is of the formula —(CH$_2$)$_n$—CO—R17 in which n is 1 to 4 and R17 is (1–4C)alkyl, phenyl or benzyl, or —R12 is of the formula —COR18 or —(CH$_2$)$_n$—OCO—R18 in which n is 1–4 and R18 is hydrogen, (1–4C)alkyl, (1–4C)haloalkyl, phenyl or benzyl, or —R12 is of the formula —G—CH$_2$—R19 in which G is carbonyl or a direct bond and R19 is phthalimido, or —R12 is of the formula —NR20R21R22 in which R20, R21 and R22 are (1–4C)alkyl, or R20 is (1–4C)alkyl and R21 and R22 are joined to form a (3–6C)carbocyclic ring, or R20, R21 and R22 are joined to form a 1-azonia-4-azabicyclo[2,2,2]octane or 1-azonia-3,5,7-triazatricyclo[3,3,1,1$^{3,7}$]decane, or —R12 is of the formula XII in which p is 1 or 2 and R23 and R24 are hydrogen or (1–4C)alkyl, or —R12 is of the formula —P(O)R25R26 in which R25 is hydroxy, (1–4C) alkoxy, (2–8C)dialkylamino, phenoxy, phenylamino or one of the values given above for R15, and R26 is (1–4C)alkyl, (1–4C)alkoxy, (2–8C)dialkylamino, phenoxy, phenylamino, piperidinyl, pyrrolidinyl, morpholinyl, piperazinyl or N-methylpiperazinyl, or —R12 is of the formula —CH$_2$P(O)R27R28 in which R27 and R28 are hydroxy or (1–4C)alkoxy, or —R12 is of the formula —CH(SR29)COOR30 in which R29 is (1–4C)alkyl and R30 is hydrogen or (1–6C)alkyl, or —R12 is of the formula XIII in which m is 0–3, R31 is hydrogen, (1–3C)alkyl or methylthio, R32 is hydrogen, (1–3C)alkyl, (3–7C)cycloalkyl, cyano, carboxy, (2–5C)carboxyalkyl or methanesulphonylamino, or phenyl optionally substituted by amino or hydroxy, or R31 and R32 are joined to form, together with the carbon to which they are attached, a (3–7C)carbocyclic ring and R33 is hydroxy, amino, (1–4C)alkoxy, (1–4C)alkylamino, phenylamino or of the formula R15 given above or of the formula NHOR34 in which R34 is hydrogen, (1–4C)alkyl, phenyl or benzyl, or —R12 is of the formula XIV in which q is 2 or 3 and R35 is hydrogen or (1–6C)alkyl, or —R12 is of the formula XV in which p is 1 or 2, R36 is hydrogen or (1–6C)alkyl and R37 and R38, which are carbon-linked, are selected from hydrogen, (1–6C)alkyl and nitro and in which (CH$_2$)$_p$ can be linked to the imidazole ring via nitrogen [(CH$_2$)$_p$ replacing R36] or carbon, provided that when R12 contains phenyl, and unless otherwise stated, the phenyl is optionally substituted by 1 or 2 groups selected from halogen, hydroxy, amino, carboxy, nitro, carbamoyl, cyano and aminomethyl;

R13 is hydrogen or of the formula R39-Y- in which Y is a direct bond or of the formula S(O)$_p$ in which p is 1 or 2 and R39 is (1–6C)alkyl or (3–8C)cycloalkyl each optionally substituted by (1–6C)alkyl, (1–6C)alkoxy, (1–6C)alkylthio, (1–6C)alkylamino, (2–8C)dialkylamino, (2–6C)alkoxycarbonyl or phenyl, the phenyl itself being optionally substituted by halogen, (1–6C)alkyl, (1–6C)alkoxy, (1–6C)alkylthio, (1–6C)alkylamino, (2–8C)dialkylamino or (2–6C)alkoxycarbonyl, or R39 is phenyl optionally substituted by one to four substituents selected from halogen, (1–6C)alkyl, hydroxy, trifluoromethyl, nitro, cyano, (1–6C)alkoxy, (1–6C)alkylthio, carboxy, (2–6C)alkoxycarbonyl, carbamoyloxy and sulpho, or R39 is a moncyclic or bicyclic heterocyclic aromatic ring system composed of 5 and/or 6 membered rings and containing 1 to 4 heteroatoms selected from oxygen, nitrogen and sulphur, said heterocyclic system being optionally substituted by halogen, (1–6C)alkyl, (1–6C)alkoxy, (1–6C)alkylthio, (1–6C)alkylamino, (2–8C)dialkylamino or (2–6C)alkoxycarbonyl, and when Y is of the formula $S(O)_p$ R39 may also be hydroxy, or R13 is halogen, cyano, carbamoyl, (1–6C)alkylthio or (1–6C)alkoxycarbonimidoyl, or —R13 is of the formula —Z—R40 in which Z is oxygen or sulphur and R40 is hydrogen or (1–6C)alkyl or (2–6C)alkenyl each of which is optionally substituted by one or two substituents selected from hydroxy, cyano, carbamoyl and COOR41 in which R41 is hydrogen, (1–6C)alkyl, acetoxymethyl, t-butyl, diphenylmethyl, p-methoxybenzyl, p-introbenzyl, triphenylmethyl or tri(1–4C)alkylsilyl;

R14 is phenyl, benzthienyl or naphthyl, each optionally substituted on a benzene ring by halogen, hydroxy, nitro, amino, methylenedioxy, (1–4C)alkyl, (1–4C)alkoxy, (1–4C)alkanoylamino or (1–4C)alkylsulphonylamino, or R14 is furyl, thienyl or cyclohexa-1,2,4,5-dienyl;

R2 is hydrogen, methoxy or formylamino;

R3 is carboxy or a biodegradeable ester thereof;

R4 is of the formula —NR42R43 in which

R42 is hydrogen, (1–4C)alkyl or benzyl;

—R43 is a non-positively charged heterocycle of the formula XVI, XVII, XVIII, XIX, XX, XXI, XXII, XXIII, XXIV, XXV, XXVI or XXVII in which $R^{44}$ and $R^{45}$ are selected from hydrogen and (1–6C)alkyl;

R46 is hydrogen, (1–6C)alkyl, (2–6C)carboxyalkyl, (1–6C)sulphoalkyl, (2–6C)aminoalkyl, (1–4C)alkylamino(2–6C)alkyl, (2–8C)dialkylamino(1–6C)alkyl, (2–6C)hydroxyalkyl or (1–6C)sulphoaminoalkyl;

R47 and R48 are selected from hydrogen, cyano, (1–6C)alkyl, hydroxy, carboxy, and (2–6C)carboxyalkyl, provided that at least one of R47 and R48 is hydroxy, carboxy or carboxyalkyl;

and the pharmaceutically-acceptable base-addition salts thereof.

It is to be understood that in the above formula I and throughout this specification, the illustrated stereochemistry of the ceph-3-em nucleus, and its optional modifications at the 1-position, is the absolute configuration.

Particular values for R5 and R6, same or different, are hydrogen, chlorine, bromine, cyano, hydroxy, carboxy, pyridyl, methyl, aminomethyl, hydroxymethyl, methoxycarbonyl, methylaminomethyl or dimethylaminomethyl, or phenyl optionally substituted by 1 or 2 radicals selected from halogen, nitro, amino, hydroxy, carboxy, cyano, methyl and methoxycarbonyl.

A particular value for R7 is carboxy, methoxycarbonyl, benzyloxycarbonyl, carbamoyl, methylcarbamoyl, dimethylcarbamoyl, carazolyl, cyano or methoxycarbonylamino.

A particular value for R8 is hydrogen, methyl, methoxy, acetyl, methylthio, methanesulphinyl, methanesulphonyl, phenyl, benzoyl, carboxy, methoxycarbonyl, benzyloxycarbonyl, carbamoyl, carbazolyl, cyano, allyl, sulphamoyl, methoxymethyl, carboxymethyl, benzyl, 4-hydroxyphenyl, 4-methoxyphenyl, pyridyl or 2-methylthio-1,3,4-thiadiazol-5-yl;

A particular value for R9 is hydrogen, methyl or phenyl.

The group of compounds of formula I in which R1 is of the formula VI constitute a preferred aspect of the invention.

A particular value for R12 is hydrogen, methyl ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, triphenylmethyl, 2-chloroethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)ethyl, tetrahydropyran-2-yl, thietan-3-yl or 2-oxo-tetrahydrofuran-3-yl, or of the formula —$(CH_2)_n$—R15 in which n is 1 to 4 and R15 is piperidino, pyrolidino, morpholino, piperazino or N-methylpiperazino, each value of R15 being optionally substituted by methyl, phenyl or benzyl, or of the formula —$(CH_2)_m$—W—R16 in which m is 0 to 3, W is sulphur or a direct bond and R16 is phenyl, pyridiniomethylene, 2-pyridinioethylene or R16 is pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, each value of R16 being optionally substituted, where possible, by one or two groups selected from methyl, amino, hydroxy, carboxy, carbamoyl, nitro, methoxycarbonyl, ethoxycarbonyl, cyano or sulpho, or of the formula —$(CH_2)_n$—CO—R17 in which n is 1 to 4 and R17 is methyl, ethyl, phenyl or benzyl, or of the formula —COR18 or —$(CH_2)_n$—OCO—R18 in which n is 1–4 and R18 is hydrogen, methyl, chloromethyl, bromomethyl, 2-chloroethyl, 2-bromoethyl, phenyl or benzyl, or of the formula —G—CH₂—R19 in which G is carbonyl or a direct bond and R19 is phthalimido, or of the formula —NR20R21R22 in which R20, R21 and R22 are methyl or ethyl, or R20 is methyl or ethyl and R21 and R22 are joined to form a cyclopropyl, cyclobutyl, cyclopentyl or cyclohexyl ring, or R20, R21 and R22 are joined to form a 1-azonia-4-azabicyclo[2,2,2]octane or 1-azonia-3,5,7-triazatricyclo[3,3,1,1³,⁷]decane, or of the formula XII in which p is 1 or 2 and R23 and R24 are hydrogen or methyl, or of the formula —P(O)R25R26 in which R25 is hydroxy, methoxy, ethoxy, dimethylamino, diethylamino, phenoxy, phenylamino, or one of the particular values given above for R15, and R26 is methyl, ethyl, methoxy, ethoxy, dimethylamino, diethylamino, phenoxy, phenylamino, piperidino, pyrrolidino, morpholino, piperazino or N-methylpiperazino, or of the formula —CH₂P(O)R27R28 in which R27 and R28 are hydroxy, methoxy or ethoxy, or of the formula —CH(SR29)COOR30 in which R29 is methyl or ethyl and R30 is hydrogen, methyl, ethyl or isopropyl, or of the formula XIII in which m is 0-3, R31 is hydrogen, methyl or methylthio, R32 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R31 and R32 are joined to form, together with the carbon to which they are attached, a cyclopropane, cyclobutane, cyclopentane, cyclohexane or cycloheptane ring and R33 is hydroxy, amino, methoxy, ethoxy, methylamino, ethylamino, phenylamino or one of the particular values for R15 given above or of the formula NHOR34 in which R34 is hydrogen, methyl, ethyl, phenyl or benzyl, or of the formula XIV in which q is 2 or 3 and R35 is hydrogen or methyl, or of the formula XV in which p is 1 or 2, R36 is hydrogen or methyl, and R37 and R38, which are carbon linked, are selected from hydrogen, methyl and nitro and in which $(CH_2)_p$ can be linked to the imidazole ring via nitrogen [$(CH_2)_p$ replacing R36] or carbon, provided that when R12 contains phenyl, and unless otherwise stated, the phenyl is optionally substituted by 1 or 2 groups selected from fluoro, chloro, bromo, hydroxy, amino, carboxy, nitro, carbamoyl, cyano and aminomethyl.

A particular value for R13 is hydrogen or of the formula R39-Y- in which Y is a direct bond or of the formula $S(O)_p$ in which p is 1 or 2, and R39 is methyl, ethyl, cyclobutyl, cyclopentyl or cyclohexyl, each optionally substituted by methyl, methoxy, methylthio, methylamino, dimethylamino, methoxycarbonyl or phenyl, the phenyl itself being optionally substituted by fluorine, chlorine, bromine, methyl, methoxy, methylthio, methylamino, dimethylamino or methoxycarbonyl, or phenyl optionally substituted by one to four substituents selected from fluorine, chlorine, bromine, methyl, hydroxy, trifluoromethyl, nitro, cyano, methoxy, methylthio, carboxy, methoxycarbonyl, carbamoyloxy and sulpho, or thiophene, furan, imidazole, thiazole, pyridine, pyrimidine, benzthiophene or benzfuran, each optionally substituted by fluorine, chlorine, bromine, methyl, methoxy, methylthio, methylamino, dimethylamino or methoxycarbonyl, and when Y is of the formula $S(O)_p$R39 may also be hydroxy, or R13 is chlorine, bromine, carbamoyl, methylthio, ethylthio or O-methylcarboxyimidoyl, or R13 is of the formula —Z—R40 in which Z is oxygen or sulphur and R40 is hydrogen or methyl, ethyl isopropyl or ethenyl, each of which is optionally substituted by one or two substituents selected from hydroxy, cyano, carbamoyl and COOR41 in which R41 is hydrogen, methyl, acetoxymethyl, t-butyl, diphenylmethyl, p-methoxybenzyl, p-nitrobenzyl, triphenylmethyl or trimethylsilyl, A particular value for R14 is phenyl, benzthienyl or naphthyl, each of which is optionally substituted on a benzene ring by fluorine, chlorine, bromine, hydroxy, nitro, amino, methylenedioxy, methyl, methoxy, acetylamino or methylsulphonylamino, or R14 is furyl, thienyl or cyclohexa-1,2,4,5-dien-1-yl.

A particular value for R3 is carboxy, COOCHR49OCOR50, COOCHR49SCOR50, COOCHR49COR50, COOCHR49OR50, COOCOOR49, COOCHR49OCOOR50, COOCH2CH2NR50R50, COOCHR49OCH2CH2OCH3, COOCH2OCO(CH2)$_t$—CHR51—NH2 or of the formula XXVIII, XXIX or XXX in which t is 0 or 1, R49 is hydrogen or methyl, R50 is hydrogen, methyl, ethyl or i-butyl, R51 is hydrogen, methyl, ethyl, n-propyl, i-propyl or t-butyl, R52 is methyl, ethyl, phenyl or benzyl, R53 is hydrogen or one, two or three radicals selected from chlorine, bromine, nitro, methyl, methoxy, methylthio, methanesulphinyl, methanesulphonyl, methoxycarbonyl, methoxythiocarbonyl, acetylamino, phenyl, phenoxy, phenylthio, benzenesulphinyl, benzenesulphonyl, phenoxycarbonyl, phenylthiocarbonyl or phenoxythiocarbonyl, R54 is hydrogen or one of the values given for R53 and R55 is hydrogen or one, two or three radicals selected from chlorine, bromine, methyl and methoxy.

A particular value for R42 is hydrogen, methyl or benzyl.

A particular value for R44 and R45 is hydrogen or methyl.

A particular value for R46 is hydrogen, methyl, ethyl, carboxymethyl, 2-carboxyethyl, 3-carboxypropyl, 1-sulphomethyl, 2-sulphoethyl, 3-sulphopropyl, 2-aminoethyl, 2-methylaminoethyl, 2-dimethylaminoethyl, 2-hydroxyethyl, sulphoaminomethyl, 2-sulphoaminoethyl or 3-sulphoaminopropyl.

A particular value for R47 or R48 is hydrogen, cyano, methyl, hydroxy, carboxy or carboxymethyl, provided that at least one of R47 and R48 is hydroxy, carboxy, or carboxymethyl.

A particular base which affords a pharmaceutically-acceptable cation is, for example, a base containing an alkali metal (e.g. sodium or potassium), or an alkaline earth metal (e.g. calcium or magnesium) or a primary, secondary or tetiary organic amine (e.g. triethylamine, morpholine, N-methylpiperidine, N-ethylpiperidine, procaine, dibenzylamine or N,N$^1$-dibenzylethylenediamine) or other amine which has been used to form salts with cephalosporins.

The following is a list of preferred features of the cephalosporin derivative of the invention. When any one of these features is taken, either singly or in combination, with the other general or particular features of the cephalosporin derivative of the invention listed above, there are obtained preferred sub-groups of compounds.

1. X is sulphur;
2. $R^1$ is of the formula VI;
3. $R^2$ is hydrogen;
4. $R^3$ is carboxy;
5. $R^{11}$ is 2-aminothiazol-4yl;
6. $R^{12}$ is (1–6C)alkyl, (3–6C)alkenyl, (3–6C)alkynyl, (3–8C)cycloalkyl, (3–6C)cycloalkyl(1–3C)alkyl, (1–3C)haloalkyl, (1–5C)cyanoalkyl, (2–6C)hydroxyalkyl, (1–4C)alkoxy(2–4C)alkyl, (2–6C)aminoalkyl or benzyl;
7. $R^{12}$ is methyl, ethyl, i-propyl, allyl, propargyl, cyclopentyl, cyclopropylmethyl, 2-chloroethyl, 2-bromoethyl, cyanomethyl, 2-cyanoethyl, 2-hydroxyethyl, 2-ethoxyethyl or benzyl;
8. $R^{12}$ is of the formula XIII;
9. In formula XIII m is 0;
10. In formula XIII $R^{33}$ is hydroxy or (1–4C)alkoxy;
11. In formula XIII $R^{31}$ and $R^{32}$ are both hydrogen or (1–3C)alkyl or $R^{31}$ and $R^{32}$ are joined to form, together with the carbon atom to which they are attached, a (3–7C)carbocyclic ring;
12. In formula XIII $R^{31}$ and $R^{32}$ are both hydrogen or methyl or $R^{31}$ and $R^{32}$ are joined to form, together with the carbon atom to which they are attached, a cyclobutyl or cyclopentyl ring;
13. $R^4$ is of the formula XXIII;
14. In the formula XXIII $R^{45}$ is methyl;
15. $R^4$ is of the formula XVI;
16. In the formula XVI $R^{44}$ is methyl;
17. $R^4$ is of the formula XXVI;
18. In the formula XXVI $R^{47}$ is carboxy;
19. In the formula XXVI $R^{48}$ is hydroxy;

Preferred compounds of the invention include those prepared in Examples 1 and 2.

The cephalosporin derivatives of the formula I may be manufactured by methods known in themselves for the manufacture of chemically analogous compounds. The following processes, R1, R2, R3, R4 and X having the meanings stated above, unless indicated otherwise, are therefore provided as further features of the invention.

The process of the invention is characterised by:
(a) reaction of a compound of the formula XXXI with a compound of the formula R43–R56 in which R56 is a displaceable radical [e.g. fluorine, chlorine, bromine, (1–6C)alkoxy, (1–6C)alkylthio, (1–6C)alkanesulphinyl or (1–6C)alkanesulphonyl];

(b) for the compounds in which R1 is of the formula III, IV, V, VI, VII or VIII, reaction of a compound of the formula XXXII with an acid, or an activated derivative thereof, derived from the acyl group of the formula III, IV, V, VI VII or VIII;

(c) for those compounds in which R1 is of the formula II, reaction of a compound of the formula XXXII with a compound of the formula XXXIII (d) for those compounds which contain one or more acidic hydroxy groups, deprotection, to form hydroxy, of the corresponding compound which carries a protecting group in place of the acidic hydrogen atom of the hydroxy group;

(e) for those compounds which contain a primary or secondary amino group, deprotection of the corresponding compound which carries a protecting group in place of the amino hydrogen;

(f) for those compounds in which X is sulphinyl, oxidation of the corresponding compound in which X is sulphur;

(g) for those compounds in which R1 is of the formula VI, reaction of a compound of the formula XXXIV with a compound of the formula R12—O—NH2;

(h) for those compounds in which R1 is of the formula VI in which R12 is other than hydrogen, reaction of a compound of the formula I in which R1 is of the formula VI in which R12 is hydrogen with a compound of the formula R56–R57 in which R56 is a displaceable radical and R57 is one of the values given above for R12, other than hydrogen; or (i) construction of the heterocyclic ring represented by R43 by standard synthetic methods. Representative examples of these standard synthetic methods are set out diagrammatically in the attached Schemes 1 and 2 in which only the substituent in the 3-position of the cephalosporin nucleus is illustrated.

The compound of the formula XXXI for use in process (a) in which R42 is hydrogen may be prepared by, for example, by reaction of a 7-amino-3-acetoxymethyl-cephalosporin with azide to give the corresponding 3-azidomethyl derivative, acylation of the 7-amino group and reduction of the 3-azidomethyl group. When R42 is alkyl or benzyl the primary amino group is then alkylated or benzylated.

The compound of the formula XXXII for use in process (b) may be prepared by reduction of the corresponding 7-amino-3-azidomethyl derivative. In this reduction it may first be necessary to protect the 7-amino group. This gives the compound of the formula XXXII in which R42 is hydrogen. As before when the compound in which R42 is alkyl or benzyl is required, the primary amino group is alkylated or benzylated.

The compound of the formula XXXIV for use in process (g) may be prepared by acylation of a compound of the formula XXXII with an acid of the formula R1—CO—COOH, or an activated derivative thereof.

The novel intermediates used to prepare the compounds of the formula I are regarded as further features of the invention.

Scheme 1

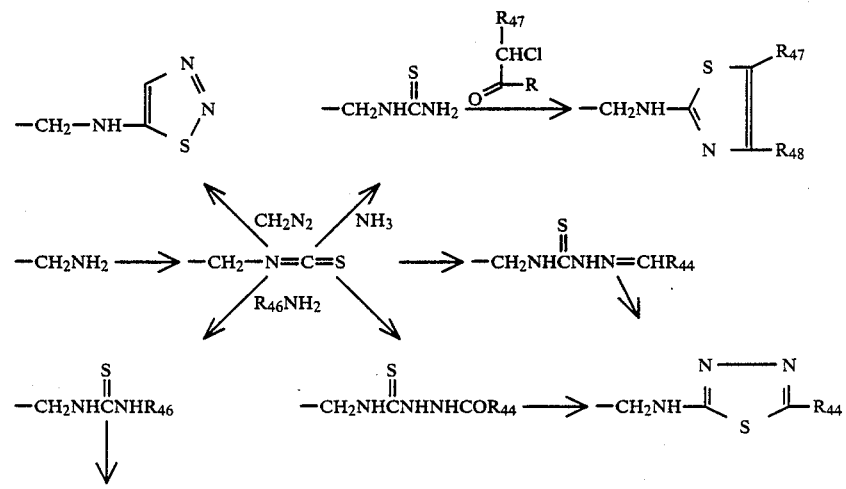

Scheme 1

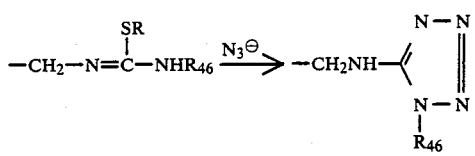

Scheme 2

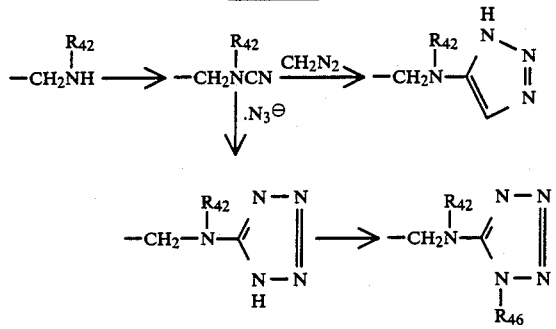

The compound of the formula XXXII is a particularly valuable intermediate of the invention.

As noted above the cephalosporin derivatives of the invention have antibacterial properties. Thus they are useful antibacterial agents, many of them having a broad spectrum of activity in vitro against standard laboratory microorganisms, both Gram-negative and Gram-positive, which are used to screen for activity against pathogenic bacteria. The antibacterial spectrum and potency of a particular compound may be determined in a standard test system. For example, the compounds of Examples 1 and 2 herein have MIC (minimum inhibitory concentration by agar-dilution technique with an inoculum size of $10^4$ CFU./spot) values of less than 1 mg/1. against representative strains of E.coli and values of 8 mg/1 and less have been recorded against strains of Staph. aureus.

Cephalosporin derivatives have generally been found to be relatively non-toxic to warm-blooded animals, and this generalisation appears to hold true for the compounds of the present invention.

According to a further feature of the invention there is provided a pharmaceutical composition which comprises a cephalosporin derivative of the invention in association with a pharmaceutically-acceptable diluent or carrier.

The pharmaceutical composition of the invention may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories and sterile injectable aqueous or oily solutions or suspensions.

In addition to the cephalosporin derivative of the formula I the pharmaceutical composition of the invention may also contain, or be co-administered with, one or more known drugs selected from other clinically useful antibacterial agents (for example other beta-lactams or aminoglycosides), inhibitors of beta-lactamase (for example clavulanic acid), renal tubular blocking agents (e.g. probenicid) and inhibitors of metabolising enzymes (for example inhibitors of peptidases, for example Z-2-acylamino-3-substituted propenoates).

A preferred pharmaceutical composition of the invention is one suitable for intravenous, subcutaneous or intramuscular injection, for example a sterile injectable containing between 1 and 10% w/w of the cephalosporin derivative, or one suitable for oral administration in unit dosage form, for example a tablet or capsule which contains between 100 mg. and 1 g. of the cephalosporin derivative.

The pharmaceutical composition of the invention will normally be administered to man in order to combat infections caused by bacteria, in the same general manner as that employed for cephalothin, cefoxitin, cephradine and other known clinically used cephalosporin derivatives, due allowance being made in terms of dose levels for the potency of the cephalosporin derivative of the present invention relative to the known clinically used cephalosporins. Thus the patient will receive a daily intravenous, subcutaneous or intramuscular dose of 0.5 to 50 g., and preferably 0.5 to 10 g., of the cephalosporin derivative, the composition being administered 1 to 4 times per day. The intravenous, subcutaneous and intramuscular dose will be given by means of a bolus injection. Alternatively the intravenous dose may be given by continuous infusion over a period of time. Alternatively each patient will receive a daily oral dose which is approximately equivalent to the daily parenteral dose. Thus a preferred daily oral dose is 0.5 to 10 g. of the cephalosporin derivative, the composition being administered 1 to 4 times per day.

The invention is illustrated, but not limited, by the following Examples. The n.m.r. spectra are quoted in delta relative to tetramethylsilane (delta=0) as internal standard, (s=singlet, d=doublet, t=triplet, q=quartet, m=multiplet, br=broad). The n.m.r. are measured at a field strength of 90 or 400 MHz. The n.m.r. solvents are as follows:
Solvent A:—$d_6$DMSO+$CD_3$COOD
Solvent B:—$d_6$DMSO+$CD_3$COOD+TFA
Solvent C:—$CDCl_3$+$CD_3$COOD
Solvent D:—$CDCl_3$+$CD_3$COOD+$CD_3$OD
The temperature are in degrees Centigrade. The following contractions are used:
TFA=trifluoroacetic acid
THF=tetrahydrofuran
HOAc=acetic acid
EtOAc=ethyl acetate
MeOH=methanol
DMF=dimethylformamide
DMSO=dimethylsulphoxide
ether=diethyl ether
HPLC=high pressure liquid chromatography

EXAMPLE 1

A solution of 7-[2-(2-aminothiazol-4-yl)-2-((Z)-methoxyimino)acetamido]-3-[(2,5-dihydro-6-diphenylmethoxy-2-methyl-5-oxo-1,2,4-triazin-3-yl)aminomethyl]ceph-3-em-4-carboxylic acid (400 mg.) in anisole/TFA (1:1 v/v; 10 ml.) was allowed to stand at ambient temperature for 20 minutes. The solvent was evaporated and the residue was dissolved in an aqueous ammonium carbonate buffer, pH6, and purified by HPLC using ammonium carbonate buffer/MeOH 92:8 v/v as eluant to give 7-[2-(2-aminothiazol-4-yl)-2-((Z)-methoxyimino)acetamido]-3-[(2,5-dihydro-6-hydroxymethyl-5-oxo-1,2,4-triazin-3-yl)aminomethyl]ceph-3-em-4-carboxylic acid (yield 25%) having the following nmr in solvent B:—3.52(s,3 H); 3.6(s, 2 H); 4.04(s, 3 H); 4.4(s, 2 H); 5.18(d,1 H); 5.84(d, 1 H); 7.1(s, 1 H).

The starting material may be obtained as follows.

To a solution of 1,2,3,6-tetrahydro-2-methyl-6-oxo-3-thio-1,2,4-triazine (200 mg.) in THF (3 ml.) was added a solution of phosgene in toluene (20% w/v; 1.5 ml.) at ambient temperature. After 20 hours the solvent was evaporated to give 2,5-dihydro-3-chloro-6-hydroxy-2-methyl-5-oxo-1,2,4-triazine [nmr in solvent C:-3.92(s, 3 H)] which was used without further purification.

The crude product from the previous stage was treated with an excess of diphenyldiazomethane in $CH_2Cl_2$ MeOH. The mixture was evaporated and the residue was purified by chromatography on silica gel using ether as eluant to give 2,5-dihydro-3-chloro-6-diphenylmethoxy-2-methyl-5-oxo-1,2,4-triazine, mp 182°–184°, nmr in $CDCl_3$:—3.76(s, 3 H); 6.74(s, 1 H); 7.2–7.5(m, 10 H).

To a solution of cefotaxime (5.24 g.) in phosphate buffer (pH 6.4, 440 ml.) was added sodium azide (2.86 g.) and sodium iodide (1.65 g.) and the mixture was immersed in a 70° bath with stirring for 4.5 hours. The solvent was evaporated to the point of precipitation and then the pH adjusted to 2.5 with 2N aqueous HCl. The resulting precipitate was collected, washed with water, acetone and ether and dried over $P_2O_5$ to give 3-azidomethyl-7-[2-(2-aminothiazol-4-yl)-2-((Z)-methoxyimino)acetamido]ceph-3-em-4-carboxylic acid in quantative yield, having the following n.m.r. in solvent A:—3.4 (d, 1 H); 3.7 (d, 1 H); 3.86 (s, 3 H); 3.95 (d, 1 H); 4.4 (d, 1 H); 5.15 (d, 1 H); 5.78 (d, 1 H); 6.75 (s, 1 H).

To a stirred suspension of Raney nickel (16 g.) in MeOH (13 ml.) at 0° was added a solution of 3-azidomethyl-7-[2-(2-aminothiazol-4-yl)-2-((Z)-methoxyimino)acetamido]ceph-3-em-4-carboxylic acid (2.96 g.) in MeOH/TFA (14 ml., 1.13 ml.). After effervescence ceased the mixture was diluted with MeOH and filtered through paper. The filtrate was evaporated, the residue purified by HPLC using water/HOAc/MeOH 79:1:20 v/v/v as eluant and the product dried over $P_2O_5$ to give 3-aminomethyl-7-[2-(2-aminothiazol-4-yl)-2-((Z)-methoxyimino)acetamido]ceph-3-em-4-carboxylic acid trifluorocetate (yield 45%) having the following n.m.r. in solvent A:—3.5–4.2 (m, 4 H); 3.9 (s, 3 H); 5.15 (d, 1 H); 5.85 (d, 1 H); 6.75 (s, 1 H). The corresponding zwitterionic form was produced by passing an aqueous solution through an ion exchange column.

A solution of 3-aminomethyl-7-[2-(2-aminothiazol-4-yl)-2-((Z)-methoxyimino)acetamido]ceph-3-em-4-carboxylic acid (200 mg.), 2,5-dihydro-3-chloro-6-diphenylmethoxy-2-methyl-5-oxo-1,2,4-triazine (160 mg.) was triethylamine (200 ul.) in DMF (4 ml.) at 0° was allowed to stand for 3.5 hours. Formic acid (1 ml.) was added and the solvent was evaporated to give 7-[2-(2-aminothiazol-4-yl)-2-((Z)-methoxyimino)acetamido]-3-[(2,5-dihydro-6-diphenylmethoxy-2-methyl-5-oxo-1,2,4-triazin-3-yl)aminomethyl]ceph-3-em-4-carboxylic acid which was used without further purification. nmr in solvent B:—3.52 (s, 3 H); 3.6 (s, 2 H); 4.04 (s, 3 H); 4.4 (s, 2 H); 5.18 (d, 1 H); 5.84 (d, 1 H); 7.1 (s, 1 H).

EXAMPLE 2

To a solution of 7-[2-(2-aminothiazol-4-yl)-2-((Z)-methoxyimino)acetamido]-3-[(3-ethylideneamino)thioureidomethyl]ceph-3-em-4-carboxylic acid in anhydrous DMF was added 2,3-dichloro-5,6-dicyanobenzoquinone (220 mg.) in two portions and the mixture was stirred at ambient temperature for 30 minutes. The mixture was poured into ether (200 ml.) and the precipitated solid collected. Purification by HPLC using an aqueous ammonium carbonate buffer pH7/MeOH 80:20 v/v as eluant gave 7-[2-(2-aminothiazol-4-yl)-2-((Z)-methoxyimino)acetamido]-3-[(5-methyl-1,2,4-thiadiazol-3-yl)methyl]ceph-3-em-4-carboxylic acid (90 mg., 22%) having the following nmr in solvent D:—2.6 (s, 3 H); 3.6 (m, 2 H); 4.18 (s, 3 H); 4.28 (d, 1 H); 4.7 (d, 1 H); 5.16 (d, 1 H); 5.94 (d, 1 H); 7.34 (s, 1 H).

The starting material may be obtained as follows.

To a solution of 3-aminomethyl-7-[2-(2-aminothiazol-4-yl)-2-((Z)-methoxyimino)acetamido]ceph-3-em-4-carboxylic acid (1.34 g.) in acetonitrile (100 ml.), water (30 ml.) and triethylamine (1.01 g.) at $-15°$ was dropwise added thiophosgene (250 ul.). The mixture was stirred for 30 minutes at $-15°$ and then the pH of the mixture was adjusted to 3–4 by addition of TFA. The solvent was evaporated and the residue purifed by HPLC using an aqueous ammonium carbonate buffer, pH 6–7/MeOH 70:30 v/v as eluant to give 7-[2-(2-aminothiazol-4-yl)-2-((Z)-methoxyimino)acetamido]3-isothiocyanatomethylceph-3-em-4-carboxylic acid having the following nmr in solvent B:—3.56 (d, 1 H); 3.84 (d, 1 H); 4.08 (s, 3 H); 4.6 (d, 1 H); 4.84 (d, 1 H); 5.3 (d, 1 H); 5.96 (d, 1 H); 7.14 (s, 1 H).

To a solution of 7-[2-(2-aminothiazol-4-yl)-2-((Z)-methoxyimino)acetamido]-3-isothiocyanatomethylceph-3-em-4-carboxylic acid in DMF (8 ml.) at ambient temperature was added acetaldehyde hydrazone (120 mg.) and the mixture was stirred for 2 hours at ambient temperature. The reaction mixture was poured into ether and the precipitate collected and purified by HPLC using aqueous ammonium carbonate buffer pH7/MeOH 80:20 v/v as eluant to give 7-[2-(2-aminothiazol-4-yl)-2-((Z)-methoxyimino)acetamido]-3-[(3-ethylideneamino)thioureidomethyl]ceph-3-em-4-carboxylic acid having the following nmr in $d_6DMSO$:—1.9 (d, 3 H); 3.64 (m, 2 H); 4.2 (m, 1 H); 4.76 (m, 1 H); 5.08 (d, 1 H); 5.72 (dd, 1 H); 6.84 (s, 1 H); 7.06 (s, 2 H); 7.54 (q, 1 H); 8.5 (m, 1 H); 9.56 (d, 1 H); 11.27 (s, 1 H).

EXAMPLE 3

7-[2-(2-aminothiazol-4-yl)-2-((Z)-1-carboxy-1-methylethoxyimino)acetamido]-3-(4-cyano-3-hydroxy-isothiazol-5-yl)aminomethylceph-3-em-4-carboxylic acid.

TFA (2 ml) was added to a suspension of 7-[2-(2-aminothiazol-4-yl)-2-((Z)-1-carboxy-1-methylethoxyimino)acetamido]-3-(4-cyano-3-diphenylmethoxyisothiazol-5-yl)aminomethylceph-3-em-4-carboxylic acid (600 mg) in anisole (2 ml), and the mixture stirred for one hour at ambient temperature. The reaction mixture was evaporated and the residue purified by HPLC eluting with a mixture of MeOH and ammonium carbonate buffer 20:80 v/v. After lyophilisation the title compound was obtained in the form of its ammonium salt (49 mg). NMR in solvent B:—1.5 (s, 3 H); 3.4–3.6 (m, 2

H); 4.1–4.3 (m, 2 H); 5.15 (d, 1 H); 5.8 (d, 1 H); 7.0 (s, 1 H).

The starting material may be obtained as follows:

A mixture of 7-[2-(2-aminothiazol-4-yl)-2-((Z)-1-carboxy-1-methylethoxyimino)acetamido]-3-aminomethyl-ceph-3-em-4-carboxylic acid (900 mg) and methyl 4-cyano-3-diphenylmethoxyisothiazol-5-sulphinate (800 mg) in solution in DMF (15 ml) containing 1 ml triethylamine was stirred at ambient temperature for five hours. The mixture was neutralised with HOAc and evaporated. The residue was purified by HPLC eluting with a 70/30 v/v mixture of methanol and water, and then with methanol to yield 700 mg of the desired product, nmr in solvent A 1.5 (s, 6 H); 3.8–4.1 (m, 2 H); 4.1–4.3 (m, 2 H); 5.15 (d, 1 H); 5.85 (d, 1 H); 7.0 (s, 1 H); 7.2–7.6 (m, 10 H).

Methyl 4-cyano-3-diphenylmethoxyisothiazol-5-sulphinate may be prepared as follows:

To a solution of 4-cyano-3-hydroxy-5-methylmercaptoisothiazole (5.1 g) obtained by the method of Hatchard, Journal of Organic Chemistry 1963, 28, 2163–2164, in a mixture of dichloromethane (100 ml) and TFA (10 ml) was added in small portions an excess of chloroperbenzoic acid (20 g) and the mixture stirred for six hours at ambient temperature. The precipitate formed was filtered and 4.8 g of methyl 4-cyano-3-hydroxyisothiazol-5-sulphinate was obtained, nmr in solvent B: 3.6 (identifying the presence of the $SO_2CH_3$ group). To a solution of the above compound (3 g) in methanol (100 ml) was added an excess of diphenyldiazomethane. After one hour at ambient temperature without stirring the methanol was evaporated and the residue purified by chromatography on $SiO_2$ eluting with dichloromethane to give 1.5 g of the desired compound, nmr in solvent B 3.4 (s, 3 H); 6.8 (s, 1 H); 7–7.5 (m, 10 H). (Upon further eluting with a mixture of dichloromethane and methanol (95:5 v/v) a by-product wherein substitution on the nitrogen atom had taken place was also isolated (1.2 g.)).

FORMULAE

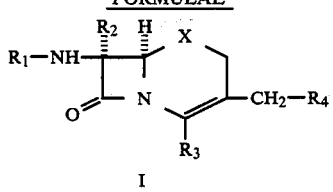

I

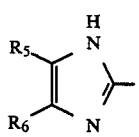

II

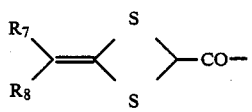

III

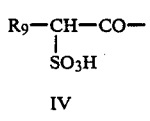

IV

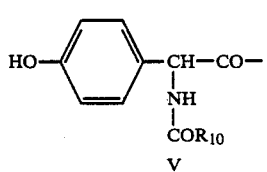

V

-continued
FORMULAE

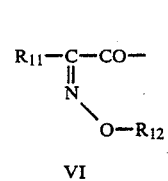

VI

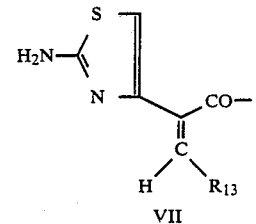

VII

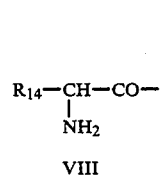

VIII

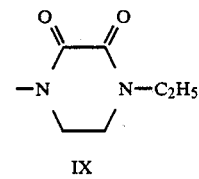

IX

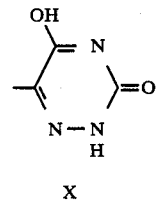

X

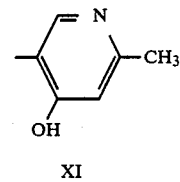

XI

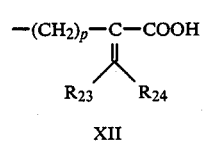

XII

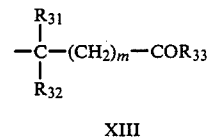

XIII

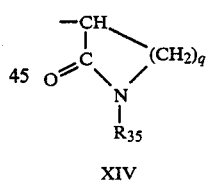

XIV

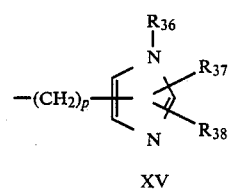

XV

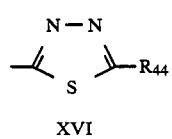

XVI

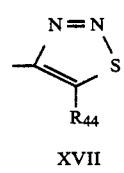

XVII

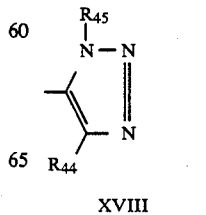

XVIII

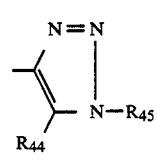

XIX 4,894,371

-continued
FORMULAE

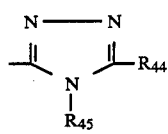
XX

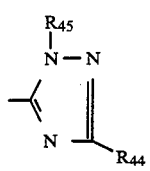
XXI

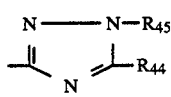
XXII

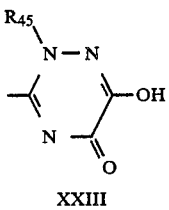
XXIII

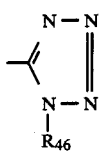
XXIV

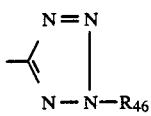
XXV

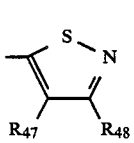
XXVI

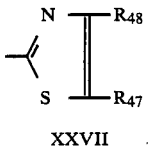
XXVII

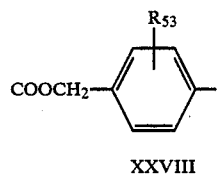
XXVIII

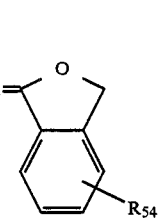
XXIX

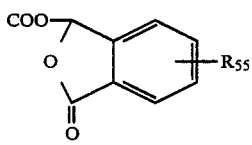
XXX

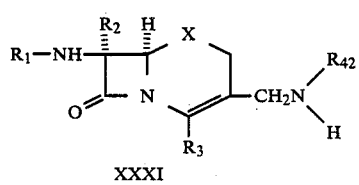
XXXI

-continued
FORMULAE

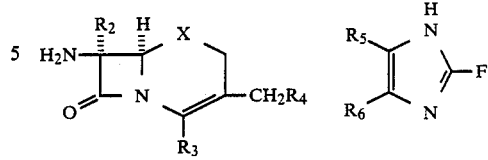
XXXII

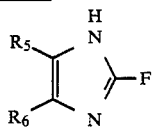
XXXIII

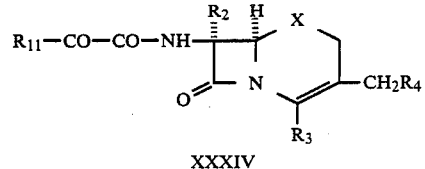
XXXIV

We claim:
1. A cephalosporin of the formula

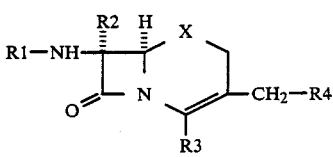
I in which
X is sulphur or sulphinyl (R or S configuration);
—R1 is of the formula

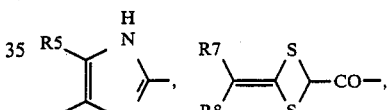
II

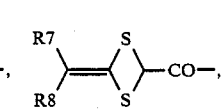
III

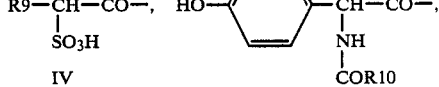
IV

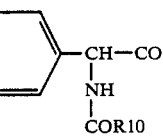
V

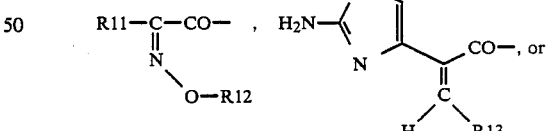
VI

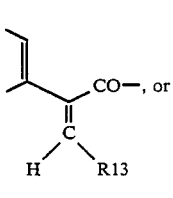
VII, or

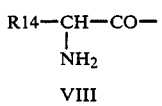
VIII in which R5 and R6, same or different, are hydrogen, halogen, cyano, hydroxy, carboxy, pyridyl, (1–6C)alkyl, (1–6C)aminoalkyl, (1–6C)hydroxyalkyl, (2–6C)alkoxycarbonyl, (2–10C)alkylaminoalkyl, (3–15C)dialkylaminoalkyl, or phenyl optionally substituted by 1 or 2 radicals selected from halogen, nitro, amino, hydroxy, carboxy, cyano, (1-6C)alkyl and (2-6C)alkoxycarbonyl;

R7 is carboxy, (2-6C)alkoxycarbonyl, benzyloxycarbonyl, carbamoyl, (2-6C)alkylcarbamoyl, (3-8C)dialkylcarbamoyl, carbazoyl, cyano or (2-6C)alkoxycarbonylamino;

R8 is hydrogen, (1-4C)alkyl, (1-4C)alkoxy, (2-5C)alkanoyl, (1-4C)alkylthio, (1-4C)-alkanesulphinyl, (1-4C)alkanesulphonyl, phenyl, benzoyl, carboxy, (2-6C)alkoxycarbonyl, benzyloxycarbonyl, carbamoyl, carbazolyl, cyano, (2-5C)alkenyl, sulphamoyl, (1-4C)hydroxyalkyl, (2-4C)carboxyalkyl, benzyl, hydroxyphenyl, [(1-4C)alkoxy]phenyl, pyridyl or (methylthio)thiadiazolyl, the point of attachment of said pyridyl or (methylthio)thiadiazolyl being a carbon atom;

R9 is hydrogen, (1-6C)alkyl or phenyl;
R10 is of the formula

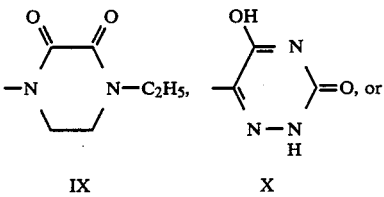

R11 is 2-aminothiazol-4-yl or 2-aminooxazol-4-yl each optionally substituted in the 5-position by fluorine, chlorine or bromine, or R11 is 5-aminoisothiazol-3-yl, 5-amino-1,2,4-thiadiazol-3-yl, 3-amino-pyrazol-5-yl, 3-aminopyrazol-4-yl, 2-aminopyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R12 is hydrogen, (1-6C)alkyl, (3-8C)cycloalkyl, (1-3C)alkyl(3-6C)cycloalkyl, (3-6C)cycloalkyl-(1-3C)alkyl, (3-6C) alkenyl, (5-8C)cycloalkenyl, (3-6C)alkynyl, (2-5C)alkylcarbamoyl, phenylcarbamoyl, benzylcarbamoyl, triphenylmethyl, (1-3C)haloalkyl, (2-6C)hydroxyalkyl, (1-4C)alkoxy(2-4C)alkyl, (1-4C)alkylthio(2-4C) alkyl, (1-4C(alkanesulphinyl(1-4C)alkyl, (1-4C)alkanesulphonyl(1-4C)alkyl, (2-6C)aminoalkyl, (1-4C)alkylamino(2-6C)alkyl, (2-8C)dialkylamino(2-6C) alkyl, (1-5C)cyanoalkyl, (1-4C)azidoalkyl, (2-5C)ureidoalkyl, 3-amino-3-carboxypropyl, 2-(amidinothio)ethyl, 2-(N-aminoamidinothio)ethyl, tetrahydropyran-2-yl, thietan-3-yl or 2-oxotetrahydrofuran-3-yl, or —R12 is of the formula —(CH2)$_N$—R15 in which n is 1 to 4 and R15 is piperidino, pyrrolidino, morpholino, piperazino or N-methylpiperazino, each value of R15 being optionally substituted by (1-4C)alkyl, phenyl or benzyl, or —R12 is of the formula —(CH2)$_m$—W—R16 in which m is 0 to 3, W is sulphur or a direct bond, and R16 is phenyl or pyridinio(1-4C)alkylene or R16 is pyridyl, imidazolyl, 1,3,4-thiadiazolyl tetrazolyl, 1-(1-4C)-alkyltetrazolyl thiazolyl, isothiazolyl or isoxazolyl in which the link with W is via a carbon or uncharged nitrogen, each value of R16 being optionally substituted, where possible, by one or two groups selected from (1-4C) alkyl, amino, hydroxy, carboxy, carbamoyl, nitro, (2-5C)alkoxycarbonyl, cyano and sulpho, or —R12 is of the formula —(CH2)$_n$—CO—R17 in which n is 1 to 4 and R17 is (1-4C)alkyl, phenyl or benzyl, or —R12 is of the formula —COR18 or —(CH2)$_N$—OCO—R18 in which n is 1-4 and R18 is hydrogen, (1-4C)alkyl, (1-4C)haloalkyl, phenyl or benzyl, or —R12 is of the formula —G—CH2—R19 in which G is carbonyl or a direct bond and R19 is phthalimido, or —R12 is of the formula

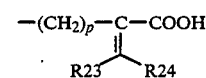

in which p is 1 or 2 and R23 and R24 are hydrogen or (1-4C)alkyl, or —R12 is of the formula —P(O)R25R26 in which R25 is hydroxy, (1-4C)alkoxy, (2-8C)dialkylamino, phenoxy phenylamino or one of the values given above for R15, and R26 is (1-4C)alkyl, (1-4C)alkoxy, (2-8C)dialkylamino, phenoxy, phenylamino, piperidinyl, pyrrolidinyl, morpholinyl, piperazinyl or N-methyl-piperazinyl, or —R12 is of the formula —CH2P(O)R27R28 in which R27 and R28 are hydroxy or (1-4C)alkoxy, or —R12 is of the formula —CH(SR29)COOR30 in which R29 is (1-4C)alkyl and R30 is hydrogen or (1-6C)alkyl, or —R12 is of the formula

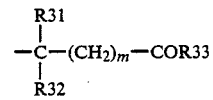

in which m is 0-3, R31 is hydrogen, (1-3C)alkyl or methylthio, R32 is hydrogen, (1-3C)alkyl, (3-7C) cycloalkyl, cyano, carboxy, (2-5C)carboxyalkyl or methanesulphonylamino, or phenyl optionally substituted by amino or hydroxy, or R31 and R32 are joined to form, together with the carbon to which they are attached, a (3-7C)carbocyclic ring and R33 is hydroxy, amino, (1-4C)alkoxy, (1-4C)alkylamino, phenylamino or of the formula R15 given above or of the formula NHOR34 in which R34 is hydrogen, (1-4C)alkyl, phenyl or benzyl, or —R12 is of the formula

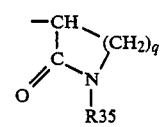

in which q is 2 or 3 and R35 is hydrogen or (1-6C)alkyl, provided that when R12 contains phenyl, and unless otherwise stated, the phenyl is optionally substituted by 1 or 2 groups selected from halogen, hydroxy, amino, carboxy, nitro, carbamoyl, cyano and aminomethyl;

R13 is hydrogen or of the formula R39-Y- in which Y is a direct bond or of the formula $S(O)_p$ in which p is 1 or 2 and R39 is (1–6C)alkyl or (3–8C)cycloalkyl each optionally substituted by (1–6C)alkyl, (1–6C)alkoxy, (1–6C)alkylthio, (1–6C)alkylamino, (2–8C)dialkylamino, (2–6C)alkoxycarbonyl or phenyl, the phenyl itself being optionally substituted by halogen, (1–6C)alkyl, (1–6C)alkoxy, (1–6C)alkylthio, (1–6C)alkylamino, (2–8C)dialkylamino or (2–6C)alkoxycarbonyl, or R39 is phenyl optionally substituted by one to four substituents selected from halogen, (1–6C)alkyl, hydroxy, trifluoromethyl, nitro, cyano, (1–6C)alkoxy, (1–6C)alkylthio, carboxy, (2–6C)alkoxycarbonyl, carbamoyloxy and sulpho, or R39 is a monocyclic or bicyclic heterocyclic aromatic ring system selected from thiophene, furan, imidazole, thiazole, pyridine, pyrimidine, benzthiophene or benzfuran, said heterocyclic system being optionally substituted by halogen, (1–6C)alkyl, (1–6C)alkoxy, (1–6C)alkylthio, (1–6C)alkylamino, (2–8C)dialkylamino or (2–6C)alkoxycarbonyl, and when Y is of the formula $S(O)_p$ R39 may also be hydroxy, or R13 is halogen, cyano, carbamoyl, (1–6C) alkylthio or (1–6C) alkoxycarboimidoyl, or —R13 is of the formula —Z—R40 in which Z is oxygen or sulphur and R40 is hydrogen or (1–6C)alkyl or (2–6C)alkenyl each of which is optionally substituted by one or two substituents selected from hydroxy, cyano, carbamoyl and COOR41 in which R41 is hydrogen, (1–6C)alkyl, acetoxymethyl, t-butyl, diphenylmethyl, p-methoxybenzyl, p-nitrobenzyl, triphenylmethyl or tri(1–4C)alkylsilyl;

R14 is phenyl, benzthienyl or naphthyl, each optionally substituted on a benzene ring by halogen, hydroxy, nitro, amino, methylenedioxy, (1–4C)alkyl, (1–4C)alkoxy, (1–4C)alkanoylamino or (1–4C)alkyl-sulphonylamino, or R14 is furyl, thienyl or cyclohexa-1,2,4,5-dienyl;

R2 is hydrogen, methoxy or formylamino;
R3 is carboxy or a biodegradeable ester thereof;
R4 is of the formula —NR42R43 in which
R42 is hydrogen, (1–4C)alkyl or benzyl;
—R43 is a non-positively charged heterocycle of the formula

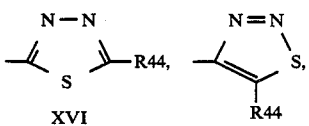 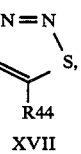
XVI  XVII

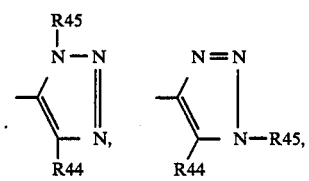 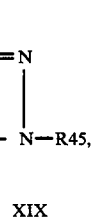
XVIII  XIX

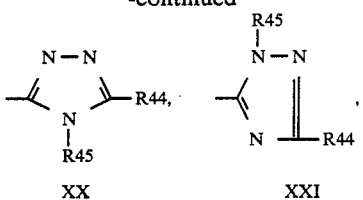
XX

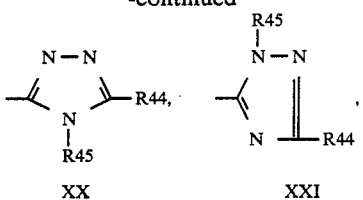
XXI

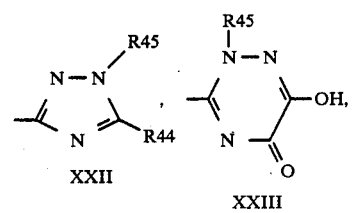
XXII

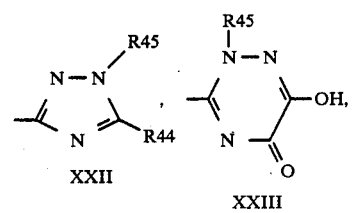
XXIII

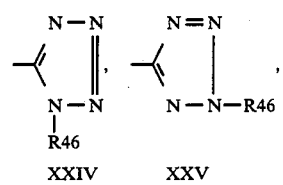
XXIV

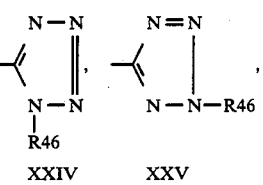
XXV

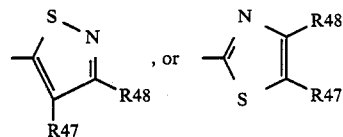 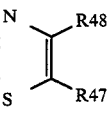
XXVI  XXVII in which R44 and R45 are selected from hydrogen and (1–6C)alkyl;

R46 is hydrogen, (1–6C)alkyl, (2–6C)carboxyalkyl, (1–6C)sulphoalkyl, (2–6C)aminoalkyl, (1–4C)alkylamino-(2–6C)alkyl, (2–8C)dialkylamino(1–6C)alkyl, (2–6C)hydroxyalkyl or (1–6C)sulphoaminoalkyl;

R47 and R48 are selected from hydrogen, cyano, (1–6C)alkyl, hydroxy, carboxy and (2–6C)carboxyalkyl, provided that at least one of R47 and R48 is hydroxy, carboxy or carboxyalkyl;

and the pharmaceutically-acceptable base addition salts thereof.

2. A compound as claimed in claim 1 in which X is sulphur, R1 is of the formula

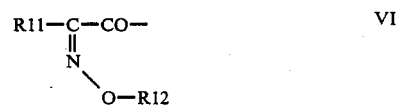
VI

R2 is hydrogen, R3 is carboxy and
R4 is of the formula —NR42R43 in which
R42 is hydrogen, (1–4C)alkyl or benzyl;
—R43 is a non-positively charged heterocycle of the formula

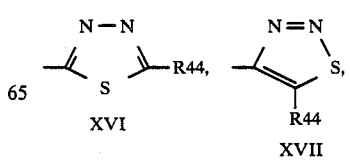 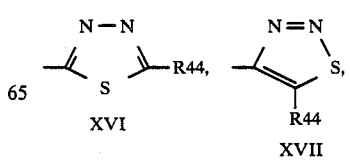
XVI  XVII

-continued

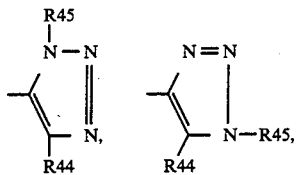

XVIII   XIX

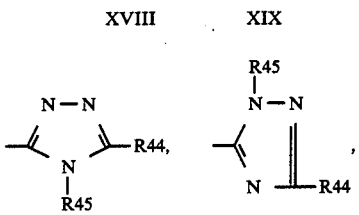

XX   XXI

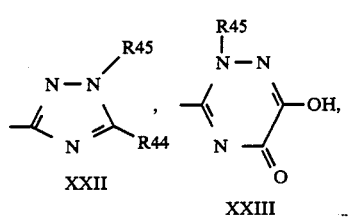

XXII   XXIII

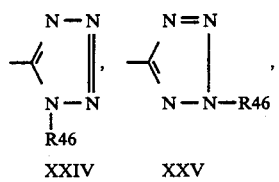

XXIV   XXV

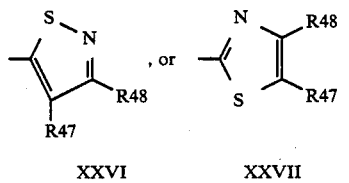

XXVI   XXVII in which R44 and R45 are selected from hydrogen and (1–6C)alkyl;

R46 is hydrogen, (1–6C)alkyl, (2–6C)carboxyalkyl, (1–6C)sulphoalkyl, (2–6C)aminoalkyl, (1–4C)alkylamino-(2–6C)alkyl, (2–8C)dialkylamino(1–6C)alkyl, (2–6C)hydroxyalkyl or (1–6C)sulphoaminoalkyl;

R47 and R48 are selected from hydrogen, cyano, (1–6C)alkyl, hydroxy, carboxy and (2–6C)carboxyalkyl, provided that at least one of R47 and R48 is hydroxy, carboxy or carboxyalkyl, 3. A compound as claimed in claim 1 in which R43 is of the formula

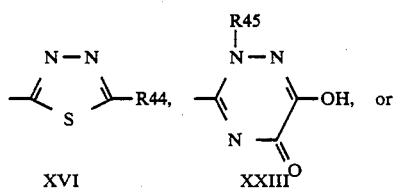

XVI   XXIII

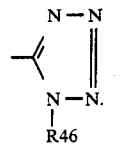

XXIV

4. A compound as claimed in claim 1 in which R43 is of the formula

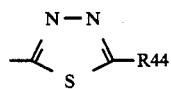

XVI in which R44 is methyl, XXIII in which R45 is methyl or XXVI in which R47 is carboxy and R48 is hydroxy.

5. A cephalosporin of the formula

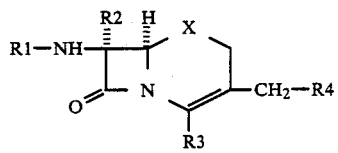

I as claimed in claim 1 in which X is sulphur or sulphinyl (R or S configuration);

—R1 is of the formula

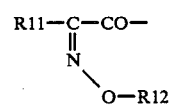

VI in which R11 is as defined in claim 1 and R12 is hydrogen, methyl, ethyl, isopropyl, t-butyl, cyclopropyl, cyclobutyl, cyclopentyl, cyclohexyl, methylcyclopropyl, methylcyclobutyl, methylcyclopentyl, methylcyclohexyl, cyclopropylmethyl, cyclobutylmethyl, cyclopentylmethyl, allyl, cyclopentenyl, cyclohexenyl, propargyl, methylcarbamoyl, ethylcarbamoyl, phenylcarbamoyl, benzylcarbamoyl, triphenylmethyl, 2-chloro-ethyl, 2-bromoethyl, 2-hydroxyethyl, 3-hydroxypropyl, 2-methoxyethyl, 2-ethoxyethyl, 2-methylthioethyl, 2-methanesulphinylethyl, 2-methanesulphonylethyl, 2-aminoaminoethyl, 3-aminopropyl, 2-methylaminoethyl, 2-dimethylaminoethyl, cyanomethyl, 2-cyanoethyl, azidomethyl, 2-azidoethyl, ureidomethyl, 3-amino-3-carboxypropyl, 2-(amidino)ethyl, 2-(N-aminoamidino)-ethyl, tetrahydropyran-2-yl, thietan-3-yl or 2-oxo-tetrahydrofuran-3-yl, or of the formula —(CH$_2$)$_n$—R15 in which n is 1 to 4 and R15 is piperidino, pyrolidino, morpholino, piperazino or N-methylpiperazino, each value of R15 being optionally substituted by methyl, phenyl or benzyl, or of the formula —(CH$_2$)$_m$—W—16 in which m is 0 to 3, W is sulphur or a direct bond and R16 is phenyl, pyridiniomethylene, 2-pyridinioethylene or R16 is pyridyl, imidazolyl, 1,3,4-thiadiazolyl, tetrazolyl, 1-methyltetrazolyl, thiazolyl, isothiazolyl or isoxazolyl in which the link with W is via a carbon or uncharged nitrogen, each value of R16 being optionally substituted, where possible, by one or two groups selected from methyl, amino, hydroxy, carboxy, carbamoyl, nitro, methoxycarbonyl, ethoxycarbonyl, cyano or sulpho, or of the formula —(CH$_2$)$_n$—CO—R17 in which n is 1 to 4 and R17 is methyl, ethyl, phenyl or benzyl, or of the formula —COR18 or —(CH$_2$)$_n$—OCO—R18 in which n is 1–4 and R18 is hydrogen, methyl, chloromethyl, bromomethyl, 2-chloroethyl, 2-bromoethyl, phenyl or benzyl, or of the formula —G—CH$_2$—R19 in which G is carbonyl or a direct bond and R19 is phthalimido, or of the formula

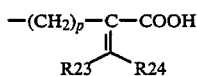

XII in which p is 1 or 2 and R23 and R24 are hydrogen or methyl, or of the formula —P(O)R25R26 in which R25 is hydroxy, methoxy, ethoxy, dimethylamino, diethylamino, phenoxy, phenylamino, or one of the particular values given above for R15, and R26 is methyl, ethyl, methoxy, ethoxy, dimethylamino, diethylamino, phenoxy, phenylamino, piperidino, pyrrolidino, morpholino, piperazino or N-methylpiperazino, or of the formula —CH$_2$P(O)R27R28 in which R27 and R28 are hydroxy, methoxy or ethoxy, or of the formula —CH(SR29)COOR30 in which R29 is methyl or ethyl and R30 is hydrogen, methyl, ethyl or isopropyl, or of the formula

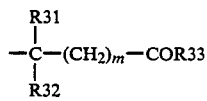

XIII in which m is 0–3, R31 is hydrogen, methyl or methylthio, R32 is hydrogen, methyl, cyclopropyl, cyclobutyl, cyclopentyl, cyclohexyl, cyano, carboxy, carboxymethyl, 2-carboxyethyl or methanesulphonylamino, or phenyl optionally substituted by amino or hydroxy, or R31 and R32 are joined to form, together with the carbon to which they are attached, a cyclopropane, cyclobutane, cyclopentane, cyclohexane or cycloheptane ring and R33 is hydroxy, amino, methoxy, ethoxy, methylamino, ethylamino, phenylamino or one of the particular values for R15 given above or of the formula NHOR34 in which R34 is hydrogen, methyl, ethyl, phenyl or benzyl, or of the formula

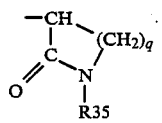

XIV in which q is 2 or 3 and R35 is hydrogen or methyl, provided that when R12 contains phenyl, and unless otherwise stated, the phenyl is optionally substituted by 1 or 2 groups selected from fluoro, chloro, bromo, hydroxy, amino, carboxy, nitro, carbamoyl, cyano and aminoethyl;

R2 is hydrogen or methoxy;

R3 is carboxy, COOCHR49OCOR50, COOCHR49SCOR50, COOCHR49COR50, COOCHR49OR50, COOCOOR49, COOCHR49OCOOR50, COOCH$_2$CH$_2$NR50R50, COOCHR49OCH$_2$CH$_2$OCH$_3$, COOCH$_2$OCO(CH$_2$)$_r$—CHR51—NH or of the formula

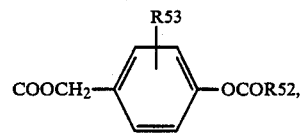

XXVIII

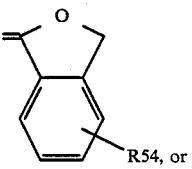

XXIX

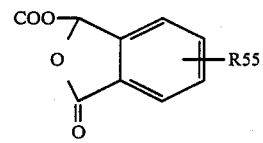

XXX in which t is 0 or 1, R49 is hydrogen or methyl, R50 is hydrogen, methyl, ethyl or i-butyl, R51 is hydrogen, methyl, ethyl, n-propyl, i-propyl or t-butyl, R52 is methyl, ethyl, phenyl or benzyl, R53 is hydrogen or one, two or three radicals selected from chlorine, bromine, nitro, methyl, methoxy, methylthio, methanesulphinyl, methanesulphonyl, methoxycarbonyl, methoxythiocarbonyl, acetylamino, phenyl, phenoxy, phenylthio, benzenesulphinyl, benzenesulphonyl, phenoxycarbonyl, phenylthiocarbonyl or phenoxythiocarbonyl, R54 is hydrogen or one of the values given for R53 and R55 is hydrogen or one, two or three radicals selected from chlorine, bromine, methyl and methoxy;

R4 is of the formula —NR42R43 in which R42 is hydrogen, methyl or benzyl and R43 is a non-positively charged heterocycle of the formula

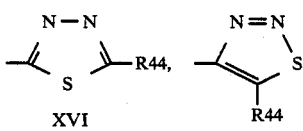

XVI     XVII

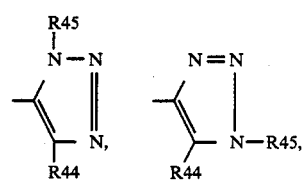

XVIII     XIX

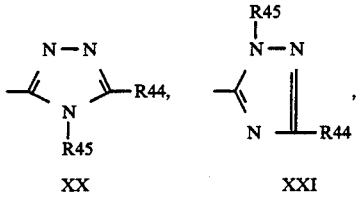

XX                XXI

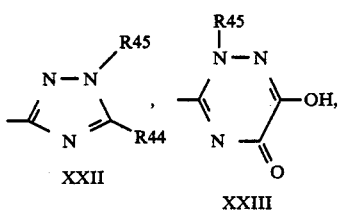

XXII              XXIII

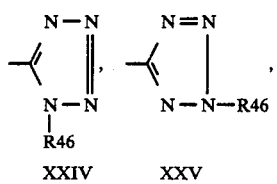

XXIV        XXV

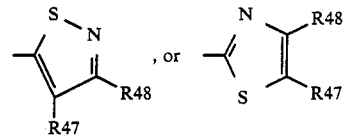

XXVI            XXVII in which R44 and R45 are hydrogen or methyl;

R46 is hydrogen, methyl, ethyl, carboxymethyl, 2-carboxyethyl, 3-carboxypropyl, 1-sulphomethyl, 2-sulphoethyl, 3-sulphopropyl, 2-aminoethyl, 2-methylaminoethyl, 2-dimethylaminoethyl, 2-hydroxyethyl, sulphoaminomethyl, 2-sulphoaminoethyl or 3-sulphoaminopropyl;

R47 and R48 are hydrogen, cyano, methyl, hydroxy, carboxy, or carboxymethyl, provided that at least one of R47 and R48 is hydroxy, carboxy or carboxymethyl;

and the pharmaceutically-acceptable base-addition salts thereof.

6. A compound as claimed in claim 1 in which R11 is 2-aminothiazol-4-yl.

7. A compound as claimed in claim 1 in which R12 is methyl, ethyl, i-propyl, allyl, propargyl, cyclopentyl, cyclopropylmethyl, 2-chloroethyl, 2-bromoethyl, cyanomethyl, 2-cyanoethyl, 2-hydroxyethyl, 2-ethoxyethyl, benzyl or of the formula XIII in which m is 0, R31 and R32 are both hydrogen or methyl or are joined to form, together with the carbon atom to which they are attached, a cyclobutyl or cyclopentyl ring and R33 is hydroxy or methoxy.

8. An antibacterial pharmaceutical composition comprising an antibacterially effective amount of a cephalosporin as claimed in claim 1 or a pharmaceutically-acceptable base-addition salt thereof in association with a pharmaceutically-acceptable diluent or carrier.

9. A method of treatment of a bacterial infection in a human or animal host which comprises administering the said host an antibacterially effective amount of a compound as claimed in claim 1.

* * * * *